(12) United States Patent
Imura et al.

(10) Patent No.: US 6,340,648 B1
(45) Date of Patent: Jan. 22, 2002

(54) CALCIUM PHOSPHATE POROUS SINTERED BODY AND PRODUCTION THEREOF

(75) Inventors: Kohichi Imura; Hideo Uemoto; Akimichi Hojo, all of Hadano; Junzo Tanaka, Tsukuba; Masanori Kikuchi, Tsukuba; Yasushi Suetsugu, Tsukuba; Hiraku Yamazaki, Tokyo; Masami Kinoshita, Tokyo; Nobuaki Minowa, Tokyo, all of (JP)

(73) Assignees: Toshiba Ceramics Co., Ltd., Tokyo; National Institute for Research in Inorganic Materials-Science and Technology Agency, Tsukuba; Toshiba Denko Co., Ltd., Tokyo, all of (JP)

( * ) Notice: Subject to any disclaimer, the term of this patent is extended or adjusted under 35 U.S.C. 154(b) by 0 days.

(21) Appl. No.: 09/548,742

(22) Filed: Apr. 13, 2000

(30) Foreign Application Priority Data

Apr. 13, 1999 (JP) ............................ 11-105579

(51) Int. Cl.$^7$ ......................... C07B 25/35; C04B 38/06; C04B 35/447
(52) U.S. Cl. ............................ 501/80; 501/1; 501/123; 501/84; 106/35; 623/16.11; 623/23.56; 623/23.61
(58) Field of Search ............................ 501/1, 123, 84, 501/80; 106/35; 623/16.11, 23.56, 23.61

(56) References Cited

U.S. PATENT DOCUMENTS

| | | | |
|---|---|---|---|
| 4,371,484 A | * | 2/1983 | Inukai et al. .................. 501/1 |
| 4,472,332 A | * | 9/1984 | Fukushima et al. ............ 501/1 |
| 4,654,314 A | * | 3/1987 | Takagi et al. ................. 501/82 |
| 4,963,145 A | * | 10/1990 | Takagi et al. ................. 606/76 |

FOREIGN PATENT DOCUMENTS

| | | | |
|---|---|---|---|
| EP | 0 253 506 | | 1/1988 |
| JP | 60-16879 | * | 1/1985 |
| JP | 60-40298 | * | 9/1985 |
| JP | 2-33388 | * | 7/1990 |
| JP | 5-33062 | * | 5/1993 |
| JP | 5-75427 | * | 10/1993 |
| JP | 5-305134 | * | 11/1993 |
| JP | 60-21763 | | 1/1994 |
| JP | 6-296676 | * | 10/1994 |
| JP | 7-291759 | * | 11/1995 |
| JP | 2576404 | * | 11/1996 |
| JP | 10-167853 | * | 6/1998 |
| WO | 93/04013 | | 3/1993 |
| WO | 98/15505 | | 4/1998 |

OTHER PUBLICATIONS

Derwent Abstract 1995–100985 Takeshi et al., "Porous Bone Filler", WPI, Document 070023994, Jan. 27, 1995.

Derwent Abstract 1995–0100903, Masahiko et al., "Production of Artificial Bone Material", WPI, Document 060296680, Oct. 25, 1994.

Derwent Abstract 1995—069296, Hideaki et al.; "Cell Culture Supporter and Culture of Osteoblast", WPI, Document 060343456, Dec. 20, 1994.

* cited by examiner

*Primary Examiner*—C. Melissa Koslow
(74) *Attorney, Agent, or Firm*—Foley & Lardner

(57) ABSTRACT

A calcium phosphate porous sintered body which comprises spherical pores communicating with one another substantially throughout the body with a porosity of 55% or more and 90% or less, and has an average diameter of the inter-pore communicating parts of 50 $\mu$m or more, a pore diameter of 150 $\mu$m or more, and a three-point bending strength of 5 MPa or more, and a method for producing the same.

14 Claims, No Drawings

CALCIUM PHOSPHATE POROUS SINTERED BODY AND PRODUCTION THEREOF

BACKGROUND OF THE INVENTION

1. Field of the Invention

This invention relates to a calcium phosphate porous sintered body usable as a substitute or repairing material for bone or tooth, carrier material for drug delivery and gradual release system and a culture (vessel) or induction vessel for bone or cartilaginous or other tissues and organs, and a method for producing the same. More specifically, it relates to a calcium phosphate porous sintered body having a porous structure excellent in characteristics such as affinity with a living body, cell and tissue intruding property necessary for bone formation, physical, chemical and biological properties and a method for producing the same.

2. Description of the Prior Art

As the materials used for artificial bone, artificial tooth and compensation of bones (hereinafter referred to as "bone filler") in dentistry, cerebral surgery and orthopaedic surgery, those nontoxic, sufficient in mechanical strength, highly affinitive with a living body so as to facilitate the direct bonding therewith, and naturally in vivo so as to be naturally replaceable by a newly formed bone are preferred.

From such a viewpoint, a bone filler having a porous structure consisting of a calcium phosphate compound has been used.

As a method for producing such a bone filler having a porous structure, it is known to mix a raw material powder with a thermally decomposable material, molding the mixture into a prescribed form, and performing the removal of the thermally decomposable material and sintering of the raw material powder by heating (Japanese Patent Laid-Open No. 60-21763, Japanese Patent Laid-Open No. 60-16879).

In these known methods, however, the contact of the thermally decomposable material added for formation of pores is not necessarily uniform, and the formed pores are mostly apt to be open cells. Even if the formed adjacent pores are in contact and continued to each other, the sectional area of the communicating part of each pore (hereinafter referred to as "communicating part") is minimized. In such a pore structure, it is difficult to make cells necessary for bone formation (osteoblasts and related cells) intrude uniformly into each pore.

As a method for increasing the sectional area of the communicating part, thus, it is known to cover the surfaces of combustible spherical particles with a binder, house an aggregate of the particles in a molding die followed by pressurization so that the surface part of each particle is fixed in a contact state with the surface of the other particles adjacently arranged around it, fill the spaces among the particles with a slurry prepared by suspending a calcium phosphate powder, which is then dried and solidified, further heat the formed body to thermally decompose and remove the combustible spherical particles and the binder, and then perform a sintering (Japanese Patent Laid-Open No. 7-291759).

The bone filler of porous structure produced according to this method has a sufficient sectional area of the communicating part.

However, in the contact fixation of the combustible spherical particles by pressurization, no consideration is given to the problem that the skeleton part constituting the porous body is apt to break because of a large contraction caused at the time of changing the filled state of the powder by the removal of moisture from the slurry, although the combustible spherical particles fixed in drying are hardly dimensionally changed, although the breakage of the porous structure by springback is taken into consideration to some degree by limiting the pressurizing force.

Further, the fixed combustible spherical particles cause high thermal expansion in the temperature rising step until the fixed combustible spherical particles are thermally decomposed and removed, while the skeleton part constituting the porous body consisting of the filled body of the raw material powder is not so much thermally expanded. Therefore, the thermal expansion difference is increased, resulting in the easy breakage of the skeleton part constituting the porous body. This problem is nor taken into consideration.

No consideration is given either to the problem that a large quantity of a gas generated in the thermal decomposition of the combustible spherical particles and the binder cannot get away to the outside, and the resulting pressure causes the cracking of the porous body inner part.

Therefore, it is difficult to reveal a sufficient mechanical strength according to such conventional methods.

SUMMARY OF THE INVENTION

This invention has an object to provide a calcium phosphate porous sintered body having a porous structure sufficient in mechanical strength and highly affinitive with a living body and comprising pores mostly uniformly laid in mutually communicating state so that osteoblasts and related calls is easy to intrude into most of the pores, and a method for producing the same.

This invention provides a calcium phosphate porous sintered body and a method for producing the same described in each claim.

DETAILED DESCRIPTION OF THE INVENTION

In a preferred mode of this invention, the calcium phosphate porous sintered body comprises spherical pores communicating with one another substantially throughout the porous sintered body. The porosity is 55% or more and 90% or less (preferably 60–85%). The average diameter of the inter-pore communicating parts is 50 $\mu$m or more (preferably, 100–4000 $\mu$m). The pore diameter is 150 $\mu$m or more (preferably, 200–5000 $\mu$m). The there-point bending strength is 5 MPa or more (preferably, 10 MPa or more).

Measurement of Porosity

The porosity of the calcium phosphate porous sintered body is measured according to the following method. A dense sintered body having the same composition as a calcium phosphate porous sintered body to be measured is preliminarily prepared, and a measurement is performed by use of a true density meter to determine the true density ($\rho^*$). The calcium phosphate porous sintered body to be measured is worked into a cube or cylinder, and the dimension is measured to determine the volume by calculation. Further, the weight is measured, and this weight is divided by the volume to determine the density ($\rho$). Using these values, the porosity (P) is calculated according to the following expression.

$$P = 1 - \rho/\rho^*$$

The calcium phosphate porous sintered body is embedded in a resin, and the resulting resin is polished and microscopically observed to determine the area ($A_p$) of the pore part and the area ($A_m$) of the part where the area of the pore part was measured by image analysis. Using these values, the porosity (P) is calculated according to the following expression.

$$=A_p/A_m$$

Measurement of Pore Diameter

The pore diameter of the calcium phosphate porous sintered body is measured according to the following method. The calcium phosphate porous sintered body is embedded in a resin, and this is polished and microscopically observed to determine the substantially spherical pore area by image analysis. The larger number of pores to be measured is more preferable from the viewpoint of precision, but 300 pores or more are generally sufficient for the measurement. Since the pore area determined herein is the section in a plane passing a part of the substantially spherical pore and not the diameter of the pore, a three-dimensional correction is performed.

As the method for correction, Johnson-Saltkov method is used. In the Johnson-Saltkov method, the diameter distribution of pores can be directly obtained from the observed area of the pores. As the average pore diameter, the pore diameter occupying 50% of the total pore volume in the accumulated distribution of the pore volume is calculated.

Since the calcium phosphate porous sintered body according to this invention has the structural characteristic as described above, it has characteristics of sufficient mechanical strength, high affinity with a living tissue so as to facilitate the coupling therewith, and natural extinction in vivo so as to be naturally replaceable with a newly formed bone.

For the use as a chemical gradually releasing base material, it has a large quantity of pores capable of sufficiently retaining a medicine and inter-pore communicating parts effective for gradually releasing the medicine, and also retains sufficient strength.

The reason for setting the porosity to 55% or more and 90% or less is described below.

With a porosity of less than 55%, the sectional area of the communicating parts formed among adjacent pores is minimized, or lot of closed cells come to existence, which makes it difficult to take a sufficient quantity of osteoblast or the like into the calcium phosphate porous sintered body of this invention in the use as the bone filler, and makes it difficult to ensure the pores capable of sufficiently retaining the medicine in the use as the chemical gradually releasing base material.

With a porosity exceeding 90%, the strength of the calcium phosphate porous sintered body is remarkably deteriorated.

The reason for setting the average diameter of the inter-pore communicating parts to 50 $\mu$m or more is that the cell intruding property necessary for bone formation can not be provided with less than 50 $\mu$m. The upper limit of the average diameter of the inter-pore communicating parts is not particularly limited, but even a diameter of about 8 mm is practicable.

The average diameter of the inter-pore communicating parts is measured by mercury penetration method. When the diameter of the communicating part is too large to apply the mercury penetration method, the sectional part of the porous sintered body is microscopically observed for the diameters of the communicating parts, and the average diameter of the inter-pore communicating parts is calculated as the area average diameter.

The reason for setting the pore diameter of the calcium phosphate porous sintered body to 150 $\mu$m or more is that the average diameter of the inter-pore communicating parts cannot be made to 50 $\mu$m or more with less than 150 $\mu$m. The upper limit of the pore diameter is not particularly limited, but even a pore diameter of about 10 mm is practicable. The preferable pore diameter is 200–5000 $\mu$m.

The reason for setting the three-point bending strength of the calcium phosphate porous sintered body to 5 MPa or more is that the mechanical strength is insufficient in desired uses of the calcium phosphate porous sintered body of this invention with less than 5 MPa. The upper limit of the three-point bending strength is not particularly limited, but even a strength of about 100 MPa is practicable.

In a preferred potassium phosphate sintered body according to this invention, the skeleton part of the calcium phosphate porous sintered body consists a substantially densed calcium phosphate sintered body, and its surface part has fine irregularities or a layer consisting of the calcium phosphate porous sintered body. Accordingly, the specific surface area of the calcium phosphate porous sintered body is 0.1 m²/g or more.

When the calcium phosphate porous sintered body is used for the bone filler or the like, a medicine assisting the bone formation is generally adsorbed. In order to provide a sufficient adsorption quantity, the specific surface area is desirably set to 0.1 m²/g or more (particularly, 0.2 m²/g or more). From this viewpoint, the skeleton part of the calcium phosphate porous sintered body consists of a substantially densed calcium phosphate sintered body, and its surface has properly fine irregularities or a layer of the calcium phosphate porous sintered body. The specific surface area is increased by such a structure of the surface part, but a remarkable reduction in strength never occurs. Therefore, a satisfactory bone filler can be provided.

In the use as bone filler, further, the existence of the fine irregularities (including pores) on the surface of the skeleton part of the calcium phosphate porous sintered body facilitates the cling and action of osteoclast or osteoblast and, in its turn, the natural extinction of the bone filler in vivo so as to be naturally replaceable by a newly formed bone. When the surface of the skeleton part of the calcium phosphate porous sintered body has the properly fine irregularities or the layer consisting of the calcium phosphate porous sintered body, the fine irregularities cling to the filled bone and effectively function. The upper limit of the specific surface area is not particularly limited, but even a specific surface area of about 100 m²/g is practicable.

The calcium phosphate porous sintered body is mainly composed of, for example, $CaHPO_4$, $Ca_3(PO_4)_2$, $Ca_5(PO_4)_3OH$, $Ca_4O(PO_4)_2$, $Ca_{10}(PO_4)_6(OH)_2$, $CaP_4O_{11}$, $Ca(PO_3)_2$, $Ca(H_2PO_4)_2$, $Ca_2P_2O_7$, $Ca(H_2PO_4)_2 \cdot H_2O$ or the like, and includes a compound of the group of calcium phosphate (compounds).

In the compound of the group of calcium phosphate constituting this calcium phosphate porous sintered body, the component Ca may be partially substituted by at least one selected from Sr, Ba, Mg, Fe, Al, Y, La, Na, K, Ag, Pd, Zn, Pb, Cd, H and other rare earth metals. The component ($PO_4$) may be partially substituted by at least one selected from $VO_4$, $BO_3$, $SO_4$, $CO_3$, $SiO_4$ and the like. Further, the component (OH) may be partially substituted by at least one selected from F, Cl, O, $CO_3$, I, and Br.

The compound of the group of calcium phosphate may be any of homogeneous solid solution, substitutional solid solution, and interstitial solid solution as well as general crystalline, and may include a nonstoichiometric defect.

The mentioned above calcium phosphate porous sintered body is produced by the method for producing a calcium phosphate porous sintered body described below.

A preferred embodiment of such a production method comprises steps of preparing a slurry by dispersing and/or dissolving a calcium phosphate powder and an organic compound, hardenable by cross-linking polymerization, in a solvent; foaming a slurry to prescribed volume by stirring and/or gas introduction with addition of foaming agent to the slurry; foaming a compact by slip-cutting after adding of cross-link agent and/or initiator to the slurry for hardening it by cross-linking of organic compact and drying the compact followed by sintering. A dispersant, a bubble-shaping agent, a thicker or the like may be added to the slurry.

As the organic compound hardenable by cross-linking polymerization, various cross-linking polymerizable materials can be used as well as polyvinyl alcohol, methyl methacrylate, and methyl cellulose. Particularly, a linear, branch or block polymer containing amino group is preferably used because it can contribute to the dispersion of the raw material powder due to its high cationic property to produce a satisfactory slurry and also provide a satisfactory cross-linked polymer by the combination use with the cross-linking agent described below.

As the cross-linking agent, any one cross-linkable of a selected cross-linking polymerizable organic compound can be used. Particularly, when the cross-linking polymerizable organic compound having amino group such as polyacrylamide, polyethylene imine, or polypropylene imine is used, an epoxy compound having two or more epoxy groups such as sorbitol polyglycydyl ether, polyglycerol polyglycydyl ether, pentaerythritol polyglycydyl ether, diglycerol polyglycydyl ether, glycerol polyglycydyl ether, polymethylolpropane polyglycydyl ether or the like is preferably used.

As the foaming agent, cationic, anionic, amphoteric, and nonionic surface active agents can be used. When the linear, branch or block polymer having amino group such as polyacrylamide, polyethylene imine, or propylene imine is selected particularly as the cross-linking polymerizable organic material, the use of the nonionic surface active agent often results in the formation of an ion complex by the difference in ionic property, which makes the foaming operation difficult. In this case, the use of the cationic surface active agent is not desirable.

The calcium phosphate porous sintered body which comprises a skeleton part consisting of a substantially densed calcium phosphate sintered body having a surface part consisting of fine irregularities or a layer consisting of the calcium phosphate porous sintered body, and has a specific surface area of 0.1 $m^2/g$ or more can be produced according to the method described below.

For example, the surface part of the skeleton part consisting of a substantially densed calcium phosphate sintered body of the calcium phosphate porous sintered body is etched with an acid to provide fine irregularities on the surface of the skeleton part. Namely, the grain boundary part of the surface of the skeleton part consisting of the substantially densed calcium phosphate sintered body is dissolved by the etching with the acid, and fine irregularities are consequently formed on the surface of the skeleton part. As the acid used for the etching, various acids can be used in addition to hydrochloric acid, sulfuric acid, nitric acid, phosphoric acid, acetic acid, and succinic acid. The pH of the etchant is not particularly specified. However, since the etching speed is varied depending on the kind and concentration of acid, the condition is regulated. In the method described herein, since an excessive etching results in a reduction in strength of the calcium phosphate porous sintered body, the etching speed is desirably set to 0.3 $m^2/g$ or less for a crystal grain size of 1 $\mu$m although it is varied depending on the size of the crystal grain constituting the calcium phosphate porous sintered body.

In the production of the calcium phosphate porous sintered body, the following etching method is preferably adapted. Namely, the acid etching step preferably consists of the step of passing the acid into the pores of the calcium phosphate porous sintered body set within an acid passage so as to shield the passage. When the calcium phosphate porous sintered body is dipped in the acid, the porous sintered body surface part is remarkably etched, while the etching of the porous sintered body inner part does not progress much. When the etching step as in this invention is adapted, a uniform etching can be easily performed to the inner part of the calcium phosphate porous sintered body.

It is further desirable to provide the step of passing ion exchange water to sufficiently wash away the acid after acid etching and performing a thermal treatment after drying to remove the acid component adsorptively left on the surface.

In another preferred embodiment of the method for producing a calcium phosphate porous sintered body of this invention, a slurry containing a calcium phosphate powder is newly adhered to the surface part of the skeleton part of the calcium phosphate porous sintered body, dried and sintered, whereby the layer of the calcium phosphate sintered body is provided on the surface of the skeleton part of the calcium phosphate porous sintered body. The newly provided layer of the calcium phosphate sintered body can be made porous or dense depending on the sintering temperature, although it is varied depending on the composition of the calcium phosphate powder. In case of the porous body, the layer of the calcium phosphate porous sintered body can be provided on the surface of the skeleton part without reducing the strength since the substantially densed skeleton part is contained in the inner part, and the specific surface area of the calcium phosphate porous sintered body of this invention can be increased. In case of the dense body, the sectional form of the calcium phosphate porous sintered body is nearly circular since the slurry is hardly adhered to the edge-shaped communicating parts. Therefore, the mechanical strength can be improved without remarkably minimizing the average diameter of the communicating parts.

The calcium phosphate powder is a powder mainly composed of, for example, $CaHPO_4$, $Ca_3(PO_4)_2$, $Ca_5(PO_4)_3OH$, $Ca_4O(PO_4)_2$, $Ca_{10}(PO_4)_6(OH)_2$, $CaP_4O_{11}$, $Ca(PO_3)_2$, $Ca_2P_2O_7$, $Ca(H_2PO_4)_2$, $Ca_2P_2O_7$, $Ca(H_2PO_4)_2$, $H_2O$ or the like, and it also includes a compound of the group of calcium phosphate.

In the compound of the group of calcium phosphate constituting this calcium phosphate powder, the component Ca may be partially substituted by at least one selected from Sr, Ba, Mg, Fe, Al, Y, La, Na, K, Ag, Pd, Zn, Pb, Cd, H and other rare earth metals. The component ($PO_4$) may be partially substituted by at least one selected from $VO_4$, $BO_3$, $SO_4$, $CO_3$, and $SiO_4$. Further, the component (OH) may be partially substituted by at least one selected from F, Cl, O $CO_3$, I and Br.

Such a compound of the group of calcium phosphate may be any of homogeneous solid solution, substitutional solid solution and interstitial solid solution as well as general crystalline, and further include a non-stoichiometric defect.

A medicine for promoting bone formation or a medicine having another effect can be adsorbed onto the surface of the calcium phosphate porous sintered body of this invention. Further, the medicine for promoting osteo genesis or the medicine having another effect may be included in the pores.

The surface of the calcium phosphate porous sintered body of this invention can be covered with an organic material with high affinity with the living body containing a protein such as collagen.

The biodegradable characteristic of the calcium phosphate porous sintered body of this invention can be controlled by controlling the crystal grain constituting the skeleton part of the calcium phosphate porous sintered body or precipitating carbonic ions in the intergranular boundary. For example, the biodegradable characteristic of gradually degrading over a period necessary for formation of a new bone, or over two months to five years in most cases, can be imparted.

In one preferred embodiment of the production method according to this invention, a calcium phosphate powder and an organic material hardenable by cross-linking polymerization are dispersed or dissolved in a solvent to prepare a slurry. Namely, the raw material powder is dispersed by use of a ball mill, and the organic material hardenable by cross-linking polymerization is dispersed or dissolved into the solvent to form the slurry. A foaming agent is added to the slurry, and the slurry is foamed to a prescribed volume by stirring and/or gas introduction to form a foamed slurry. A cross-linking agent and/or a cross-linking initiator are added to the foamed slurry followed by mixing, and the resulting mixture is introduced into a die and hardened by cross-linking polymerization to form a compact. Until the flowing property is lost by the cross-linking polymerization after foaming, the discharge of the raw material powder and the solvent occurs from the contact parts among the adjacent bubbles toward the triple points (ridge parts) or quadruple points (top parts) of the bubbles, and the liquid membrane of the contact part is broken almost simultaneously with when the slurry loses the flowing property to form inter-pore communicating parts.

This compact is dried and sintered to form a calcium phosphate porous sintered body. At that time, the drying is desirably performed under humidifying in order to prevent the cracking caused by the dimensional difference between the inside and outside of the compact by a sudden reduction in moisture. The sintering is preferably executed at a temperature of 800° C. or higher and 1300° C. or lower.

In order to uniformly cause the inter-pore communication throughout the calcium phosphate porous sintered body of this invention, the porosity is preferably set to 55% or more. The percolation phenomenon is involved in the condition for this uniform communication of the pores, and the communication can be stably caused uniformly throughout the calcium phosphate porous sintered body with a porosity of 55% or more although the communicating parts are suddenly increased from a certain porosity.

The porosity of the calcium phosphate porous sintered body is mainly determined depending on the introduction quantity of gas to the slurry, the contraction by drying, and the contraction by sintering. When the drying contraction and sintering contraction are preliminarily determined, the porosity of the calcium phosphate porous sintered body can be controlled by the introduction of the gas to the slurry.

The pore diameter of the calcium phosphate porous sintered body can be controlled according to the kind or concentration of the surface active agent to be added as the foaming agent, the viscoelasticity of the slurry, and the time until the foamed slurry loses the flowing property by cross-linking polymerization.

According to the method for producing a calcium phosphate porous sintered body of this invention, a bone filler allowing the uniform intrusion of osteoblast or the like into each pore when filled in a living body can be easily produced.

PREFERRED EMBODIMENTS OF THE INVENTION

This invention is further concretely illustrated according to preferred embodiments.

(1) PRODUCTION METHOD

EXAMPLE 1

By use of 100 g of hydroxyapatite powder as a raw material powder, 80 g of ion exchange water as a solvent, and 12 g of polyethylene imine (solid component 60%, number average molecular weight 8000–10500) as a cross-linking polymerizable organic compound, these were mixed in a ball mill for 5 hours to prepare a slurry. Further, 192 g of a slurry of the same composition was prepared, 0.8 g of polyoxyethylene lauryl ether (nonionic surface active agent) as a foaming agent was added thereto, and the resulting slurry was foamed up to 300 $cm^3$ by mechanical stirring to produce a foamed slurry. To this was added 4 g of an epoxy compound (sorbitol glycydyl ether) as a cross-linking agent followed by sufficient stirring, and the resulting mixture was introduced into a die, allowed to stand, and released from the die at the point of time when the flowing property is lost by the cross-linking, and the strength reveals to a treatable degree. After die-releasing, the resulting compact was sufficiently dried by use of a humidifying dryer and a dryer, and sintered at 1200° C.

The resulting hydroxyapatite porous sintered body had a porosity of 70%, an average pore diameter of 200 $\mu$m, and an average diameter of communicating parts of 70 $\mu$m. The three-point bending strength was 15 MPa, which was sufficient for the use as bone filler.

The specific surface area of this sample was 0.06 $m^2/g$ in measurement by BET 1-point method.

EXAMPLE 2

The hydroxyapatite porous sintered body produced according to the method of Example 1 was set in a passage so as to shield the flow, and diluted hydrochloric acid regulated to pH 3 was carried to this passage for 10 hours at a flow rate of 50 $cm^3$/min per $cm^2$ of the hydroxyapatite porous body. The resulting hydroxyapatite porous sintered body was dried at 100° C. and thermally treated at 1000° C.

As the result of observation of this sample by SEM, crystals of about 1 $\mu$m were confirmed on the surface of the substantially densed skeleton part of the hydroxyapatite porous sintered body. The grain boundary part around the crystals was etched in a depth of about 1 $\mu$m.

This hydroxyapatite porous sintered body had a porosity of 70%, an average pore diameter of 200 $\mu$m, and an average diameter of communicating part of 75 $\mu$m. The three-point bending strength was 12 MPa, which was sufficient for the use as bone filler.

The specific surface area of this sample was 0.15 $cm^2/g$ in measurement by BET 1-point method.

Accordingly, a fine irregular structure could be provided on the surface of the substantially densed skeleton part of the hydroxyapatite porous sintered body without causing a remarkable reduction in strength by acid etching to increase the specific surface area.

EXAMPLE 3

By use of 50 g of hydroxyapatite powder as a raw material powder, 100 of ion exchange water as a solvent, and 1 g of polyethylene imine (solid component 60%, number average molecular weight 8000–10500) as a binder, these were mixed in a ball mil for 5 hours to prepare a slurry.

The hydroxyapatite porous sintered body produced according to the method of Example 1 was dipped in this slurry, the excessive slurry was drained, and the draining was further executed by air blow to dry the resulting sintered body.

This process was repeated three times to produce a hydroxyapatite porous sintered body having a hydroxyapatite powder compact adhered to the surface of the skeleton part.

This was sintered at 1200° C. The resulting porous sintered body has a porosity of 65%, an average pore diameter of 200 µm, and an average diameter of communicating part of 68 µm. The three-point bending strength was 20 MPa, which was sufficient for the use as bone filler.

As the result of SEM observation of the skeleton part of this sample, the layer of a substantially densed hydroxyapatite sintered body newly added onto the surface of the skeleton part was confirmed.

Accordingly to this method, a stronger calcium phosphate porous sintered body could be produced without largely changing the mechanism constitution of Example 1.

EXAMPLE 4

By use of 50 g of hydroxyapatite powder as a raw material powder, 100 g of ion exchange water as a solvent, and 1 g of polyethylene imine (solid component 60%, number average molecular weight 8000–10500) as a binder, these were mixed in a ball mill for 5 hours to prepare a slurry.

The hydroxyapatite porous sintered body produced according to the method of Example 1 was dipped in this slurry, the excessive slurry was drained, and the draining was further executed by air blow to dry the resulting porous sintered body.

This process was repeated three times to produce a hydroxyapatite porous sintered body having a hydroxyapatite powder compact adhered to the surface of the skeleton part.

This was sintered at 1000° C. The resulting porous sintered body had a porosity of 68%, an average pore diameter of 200 µm, and an average diameter of communicating parts of 68 µm. The three-point bending strength was 15 MPa, which was sufficient for the use as bone filler.

As the result of the SEM observation of the section of the skeleton part, the layer of a substantially densed hydroxyapatite sintered body newly added onto the surface of the skeleton part was confirmed.

The specific surface area of the sample was 0.5 m$^2$/g in measurement by BET 1-point method.

By newly providing the layer of the porous apatite sintered body on the surface of the skeleton part of the hydroxyapatite porous sintered body in this way, the specific surface area of the hydroxyapatite porous sintered body could be increased without causing a reduction in strength.

In artificial bone materials formed of the calcium phosphate porous sintered bodies of Examples 1–4, the pores mutually connected by communicating parts having a sufficient section are distributed throughout the body. Accordingly, such artificial bone materials allow the intrusion of osteoblast or the like into a living body to form a new bone.

Each raw material or its addition quantity and the conditions for sintering and the like are never limited to those concretely described in Examples 1–4.

The effect of this invention is described below.

In an artificial bone material formed of the calcium phosphate porous sintered body of this invention, the pores mutually connected by the communicating parts having a sufficient sectional area are distributed throughout the body. Accordingly, this artificial bone material allows the sufficient intrusion of osteoblast or the like into the living body to form a new bone.

The calcium phosphate porous sintered body of this invention can have mutually communicating pores with a high porosity and an increased specific area, and it is useful as a chemical gradually releasable base material.

The calcium phosphate porous sintered body of this invention can be also used as a tissue induction vessel for inducing such as osseous tissue, cartilaginous tissue into and around the material in vivo and as a tissue culture vessel for culturing such as the osseous tissue, cartilaginous tissue within the material in vitro, since it has the pores and communicating holes substitutable for the roles of a Volkmann's canal for blood vessel intrusion seen in a bone and a Haversian canal necessary for supplying nutrients.

Further, compensation of an affected part can be executed by use of the calcium phosphate porous sintered body of this invention subjected to tissue induction in vivo or tissue culture in vitro.

According to the method for producing a calcium phosphate porous sintered body of this invention, the above-mentioned calcium phosphate porous sintered body of this invention can be easily produced.

What is claimed is:

1. A calcium phosphate porous sintered body having a porous structure which comprises roughly spherical pores communicating with one another substantially throughout the body with a porosity of 55% or more and 90% or less, and has an average diameter of the inter-pore communicating parts of 50 µm or more in average, a pore diameter of 150 µm or more, and a three-point bending strength of 5 MPa or more.

2. A calcium phosphate porous sintered body according to claim 1 wherein the skeleton part of the calcium phosphate porous sintered body consists of a substantially densed calcium phosphate sintered body, its surface part has fine irregularities or a layer consisting of the calcium phosphate porous sintered body, and the specific surface area of the calcium phosphate porous sintered body is 0.1 m$^2$/g or more.

3. A calcium phosphate porous sintered body according to claim 1 wherein the calcium phosphate porous sintered body is mainly composed of at least one of compounds of the calcium phosphate group consisting of $CaHPO_4$, $Ca_3(PO_4)_2$, $Ca_5(PO_4)_3OH$, $Ca_4O(PO_4)_2$, $Ca_{10}(PO_4)_6(OH)_2$, $CaP_4O_{11}$, $Ca(PO_3)_2$, $Ca_2P_2O_7$, $Ca(H_2PO_4)_2$, and $Ca(H_2PO_4)_2 \cdot H_2O$.

4. A calcium phosphate porous sintered body according to claim 3 wherein the component Ca is partially substituted by at least one selected from Sr, Ba, Mg, Fe, Al, Y, La, Na, K, Ag, Pd, Zn, Pb, Cd, H and other rare earth metals, the component ($PO_4$) is partially substituted by at least one selected from $VO_4$, $BO_3$, $SO_4$, $CO_3$, and $SiO_4$, and the component (OH) is partially substituted by at least one selected from F, Cl, O, $CO_3$, I and Br.

5. A calcium phosphate porous sintered body according to claim 1 wherein the calcium phosphate porous sintered body consists of a calcium phosphate which is any of crystalline, homogeneous solid solution, substitutional solid solution or interstitial solid solution, and can include a non-stoichiometric defect.

6. A method for producing a calcium phosphate porous sintered body which comprises steps of preparing a slurry by dispersing and/or dissolving calcium phosphate powder and an organic polymer material which is hardenable by cross-linking polymerization in a solvent; adding a foaming agent to the slurry and foaming it to a prescribed volume by stirring and/or gas introduction to lay the slurry in a foamed state; adding a cross-linking agent and/or a cross-linking initiator to the foamed slurry followed by mixing, introducing the resulting mixture to a die, and hardening it by cross-linking polymerization to form a compact; and drying the compact followed by sintering.

7. A method for producing a calcium phosphate porous sintered body according to claim 6 wherein the organic material hardenable by cross-linking polymerization is a linear, branch or block polymer containing amino group of polyacrylamide, polyethylene imine or polypropylene imine, and the cross-linking agent is an epoxidized compound having two or more epoxy groups of sorbitol polyglycydyl ether, polyglycerol polyglycydyl ether, pentaerythritol polyglycydyl ether, diglycerol polyglycydyl ether, glycerol polyglycydyl ether or polymethylolpropane polyglycydyl ether.

8. A method for producing a calcium phosphate porous sintered body according to claim 6 wherein the surface of the skeleton part of the calcium phosphate porous sintered body is etched with an acid to provide fine irregularities on the surface of the skeleton part.

9. A method for producing a calcium phosphate porous sintered body according to claim 8 wherein the etching step with the acid consists of the step of carrying the acid into the pores of the calcium phosphate porous sintered body set within an acid passage so as to block the passage.

10. The method for producing a calcium phosphate porous sintered body according to claim 6 further comprising adhering a slurry containing a calcium phosphate powder to the surface of the skeleton part consisting of a substantially densed calcium phosphate sintered body of the calcium phosphate porous sintered body, drying and sintering to provide a layer of the substantially densed calcium phosphate sintered body on the surface of the skeleton part of the calcium phosphate porous sintered body.

11. The method for producing a calcium phosphate porous sintered body according to claim 6 further comprising adhering a slurry containing a calcium phosphate powder to the surface of the skeleton part consisting of a substantially densed calcium phosphate sintered body of the calcium phosphate porous sintered body, drying and sintering to provide a layer of the calcium phosphate sintered body on the surface of the skeleton part of the calcium phosphate porous sintered body.

12. A method for producing a calcium phosphate porous sintered body according to claim 6 wherein the calcium phosphate powder is mainly composed of at least one of compounds of the calcium phosphate group consisting of $CaHPO_4$, $Ca_3(PO_4)_2$, $Ca_5(PO_4)_3OH$, $Ca_4O(PO_4)_2$, $Ca_{10}(PO_4)_6(OH)_2$, $CaP_4O_{11}$, $Ca(PO_3)_2$, $Ca(H_2PO_4)_2$, $Ca_2P_2O_7$, and $Ca(H_2PO_4)_2 \cdot H_2O$.

13. A method for producing a calcium phosphate porous sintered body according to claim 12 wherein the component Ca is partially substituted by at least one selected from Sr, Ba, Mg, Fe, Al, Y, La, Na, K, Ag, Pd, Zn, Pb, Cd, H and other rare earth metals, the component ($PO_4$) is partially substituted by at least one selected from $VO_4$, $BO_3$, $SO_4$, $CO_3$, and $SiO_4$, and the component (OH) is partially substituted by at least one selected from F, Cl, O, $CO_3$, I, and Br.

14. A method for producing a calcium phosphate porous sintered body according to claim 6 wherein the calcium phosphate powder consists of a calcium phosphate, which is any of crystalline, homogeneous solid solution, substitutional solid solution and interstitial solid solution, and can include a non-stoichiometric defect.

* * * * *